United States Patent
Noda et al.

(10) Patent No.: US 10,605,818 B2
(45) Date of Patent: Mar. 31, 2020

(54) AUTOMATED ANALYZER

(71) Applicant: HITACHI HIGH-TECHNOLOGIES CORPORATION, Tokyo (JP)

(72) Inventors: Kazuhiro Noda, Tokyo (JP); Yukinori Sakashita, Tokyo (JP); Takushi Miyakawa, Tokyo (JP); Katsuhiro Kambara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 223 days.

(21) Appl. No.: 15/740,028

(22) PCT Filed: Jul. 8, 2016

(86) PCT No.: PCT/JP2016/070225
§ 371 (c)(1),
(2) Date: Dec. 27, 2017

(87) PCT Pub. No.: WO2017/018163
PCT Pub. Date: Feb. 2, 2017

(65) Prior Publication Data
US 2018/0188275 A1    Jul. 5, 2018

(30) Foreign Application Priority Data

Jul. 27, 2015  (JP) ................................ 2015-147753

(51) Int. Cl.
*G01N 35/04* (2006.01)
*G01N 35/00* (2006.01)
(Continued)

(52) U.S. Cl.
CPC ............ *G01N 35/04* (2013.01); *G01N 35/00* (2013.01); *G01N 35/02* (2013.01); *G01N 35/025* (2013.01);
(Continued)

(58) Field of Classification Search
CPC .......... G01N 35/04; G01N 2035/0405; G01N 2035/00435; G01N 35/025; G01N 35/02; G01N 35/00
See application file for complete search history.

(56) References Cited

U.S. PATENT DOCUMENTS

2012/0328475 A1* 12/2012 Sakairi ................ G01N 35/025
                                                422/67
2012/0328490 A1   12/2012 Loehn
2013/0118118 A1*  5/2013 Kubler ................ B01L 3/50825
                                                53/381.1

FOREIGN PATENT DOCUMENTS

CN    104386629 A    3/2015
JP    06-028334 U    4/1994
(Continued)

OTHER PUBLICATIONS

Extended European Search Report received in corresponding European Application No. 16830268.5 dated Feb. 28, 2019.
(Continued)

*Primary Examiner* — Benjamin R Whatley
*Assistant Examiner* — Curtis A Thompson
(74) *Attorney, Agent, or Firm* — Mattingly & Malur, PC

(57) ABSTRACT

The purpose of the present invention is to stably hold the lid of a reagent container in an open state without being influenced by reagent container lid opening and closing operations. An automated analyzer is provided with reagent containers 116-118, a cassette 100, a reagent container lid opening and closing mechanism, and a lid holding mechanism 131. The reagent containers 116-118 accommodate the reagent and have lids 101a-101c that pivot about a pivot point. The reagent containers 116-118 are mounted on the cassette 100. The reagent container lid opening and closing mechanism opens and closes the lids 101a-101c. The lid
(Continued)

holding mechanism 131 holds the lids 101a opened by the reagent container lid opening and closing mechanism.

6 Claims, 20 Drawing Sheets

(51) Int. Cl.
*G01N 35/02* (2006.01)
*G01N 33/00* (2006.01)
*B01L 3/00* (2006.01)
*G01N 35/10* (2006.01)
*B65B 69/00* (2006.01)

(52) U.S. Cl.
CPC ................. *B01L 3/00* (2013.01); *B65B 69/00* (2013.01); *G01N 33/00* (2013.01); *G01N 35/10* (2013.01); *G01N 2035/00287* (2013.01); *G01N 2035/00435* (2013.01); *G01N 2035/0405* (2013.01)

(56) References Cited

FOREIGN PATENT DOCUMENTS

| | | |
|---|---|---|
| JP | 2009-109403 A | 5/2009 |
| JP | 2014-507256 A | 3/2014 |
| WO | 2011/074472 A1 | 6/2011 |

OTHER PUBLICATIONS

International Search Report of PCT/JP2016/070225 dated Sep. 27, 2016.

* cited by examiner

[Fig. 1]
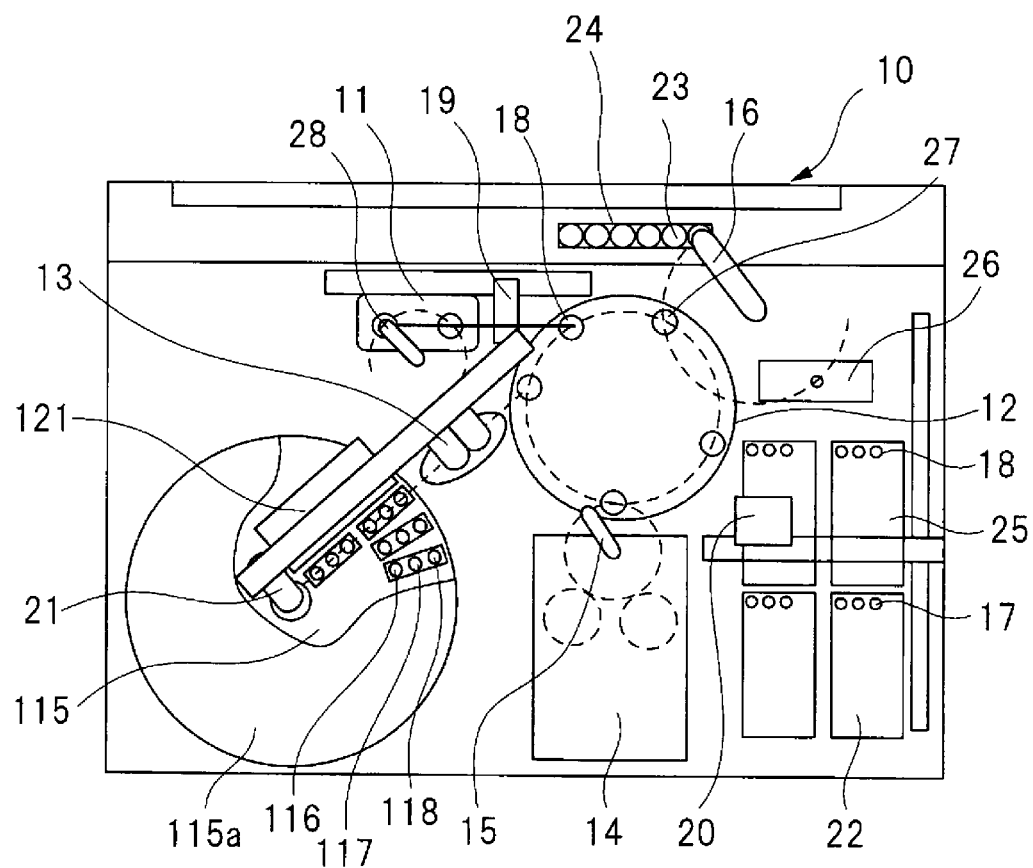

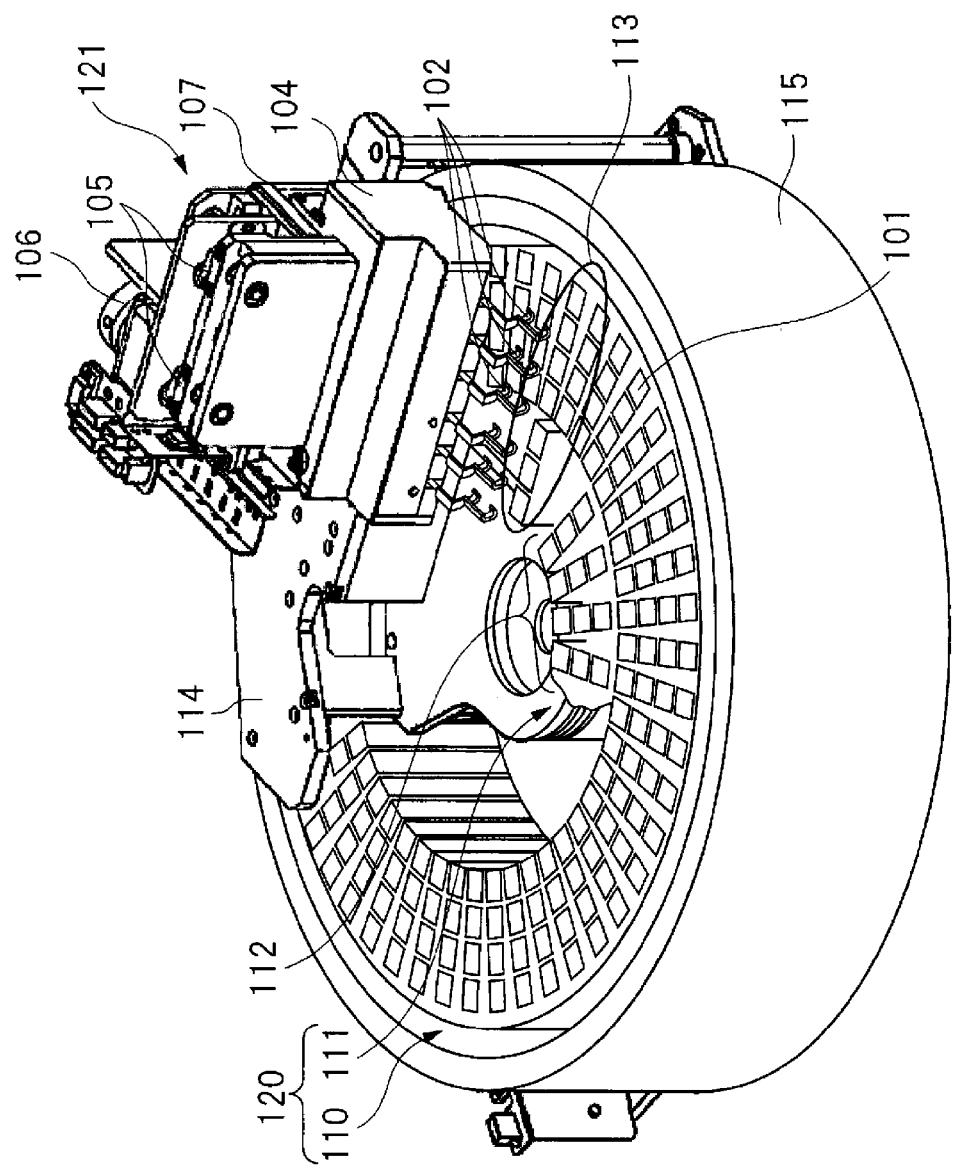
[Fig. 2]

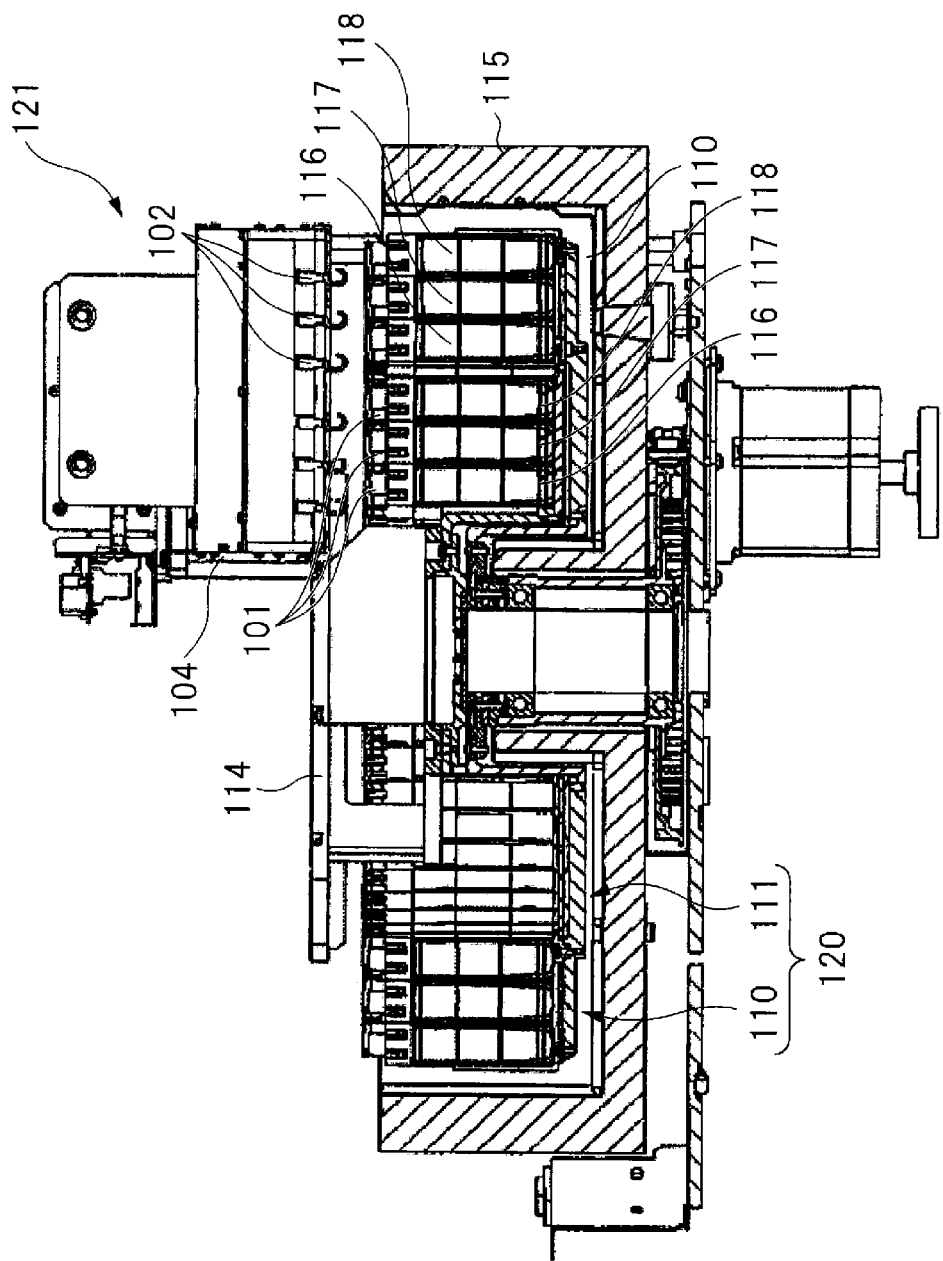
[Fig. 3]

[Fig. 4]
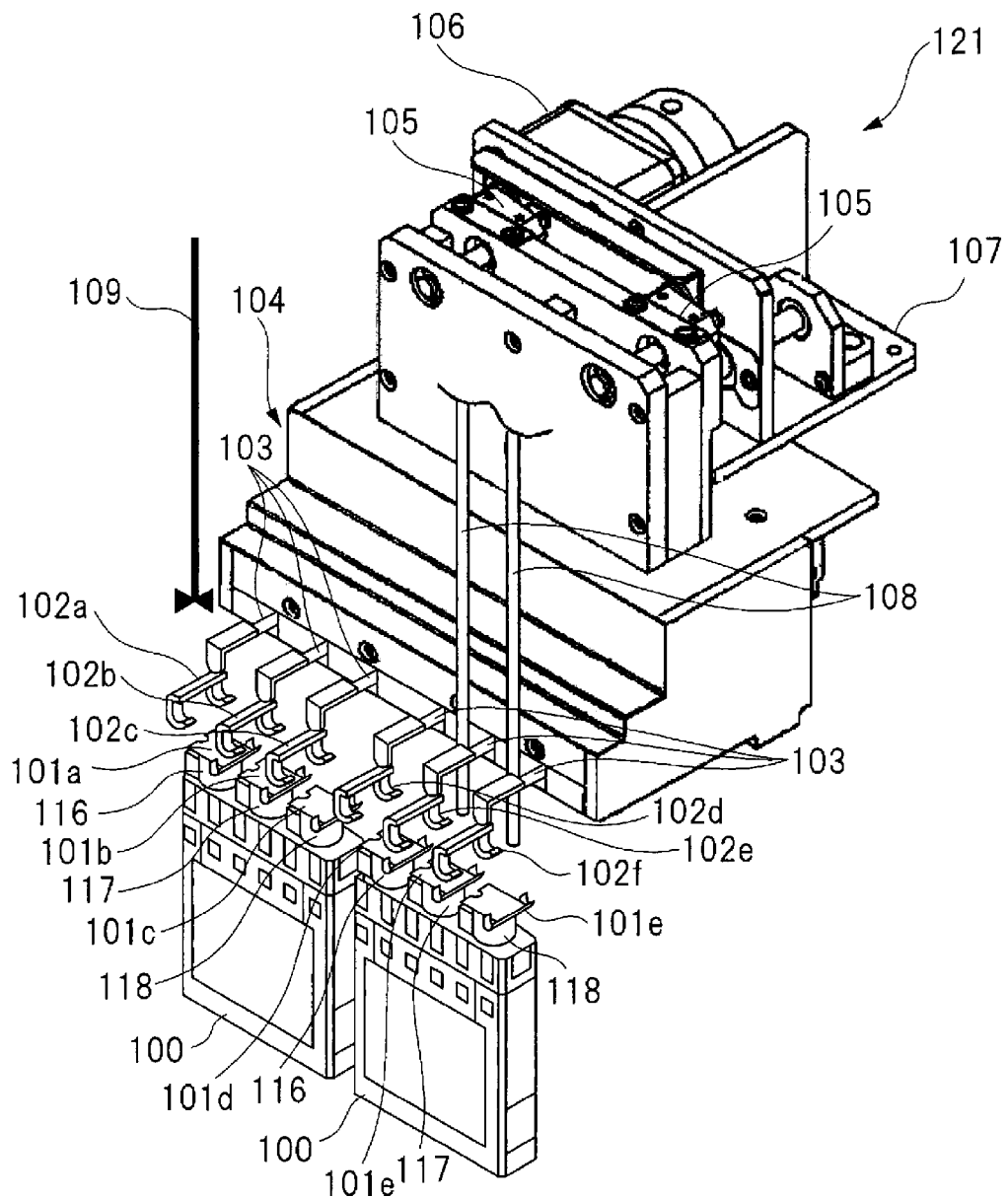

[Fig. 5]
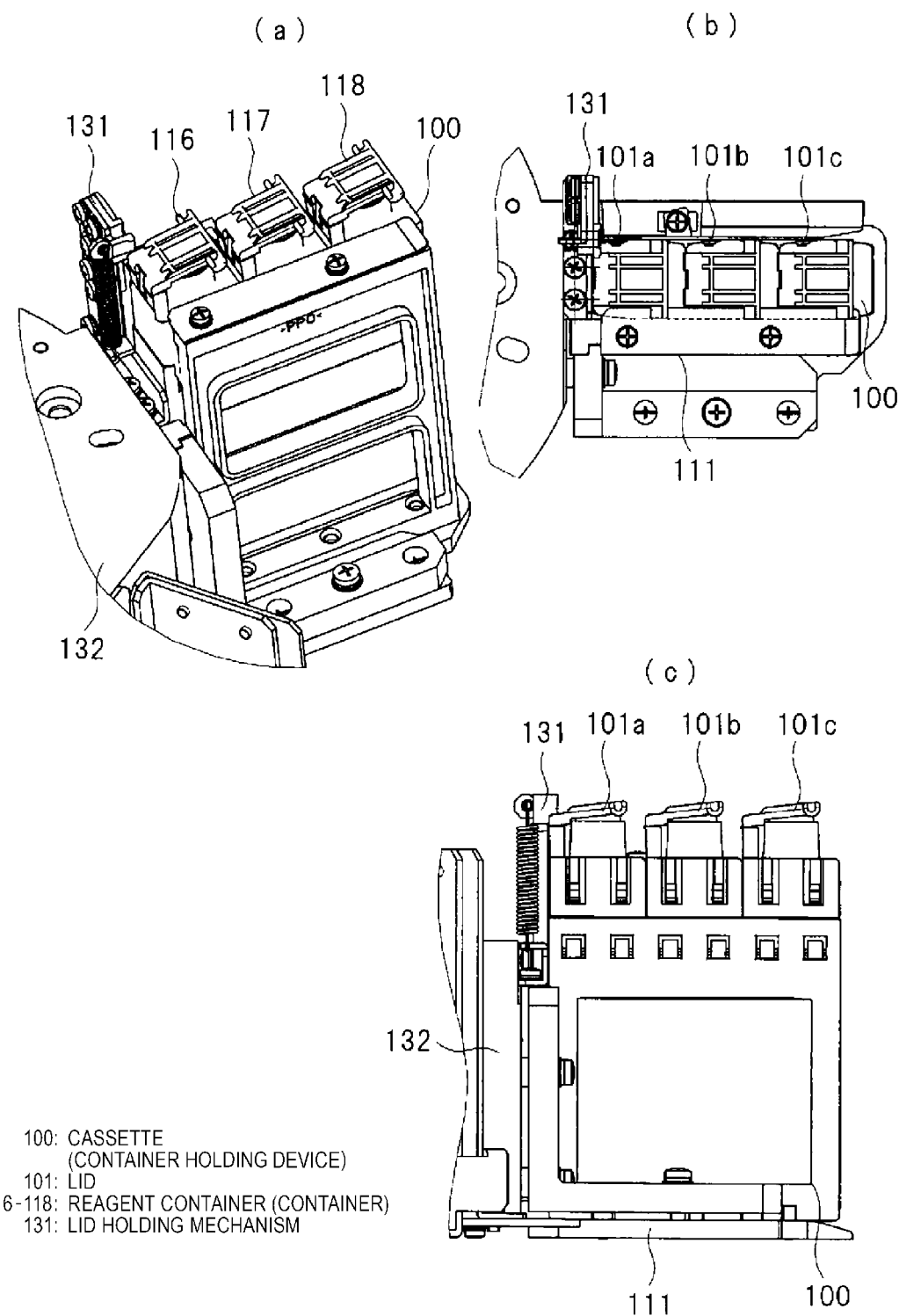

[Fig. 6]
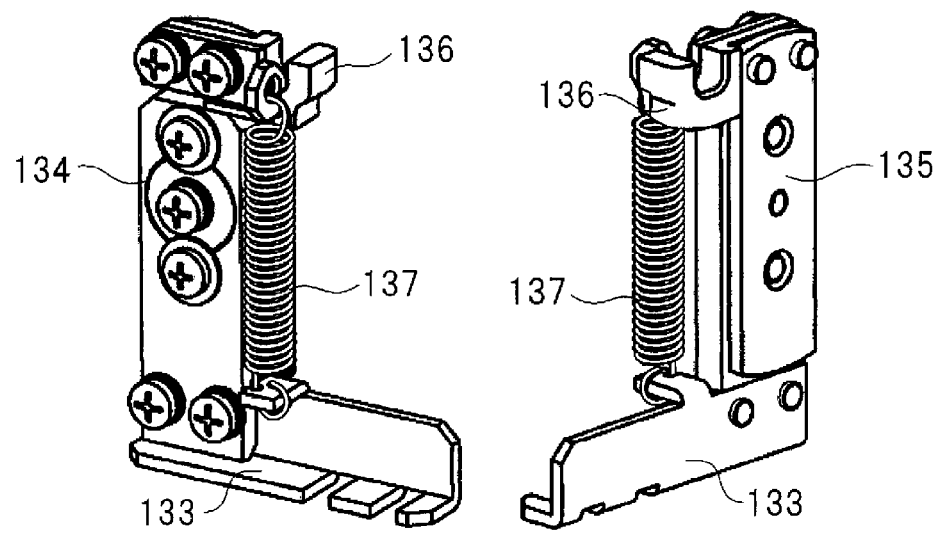
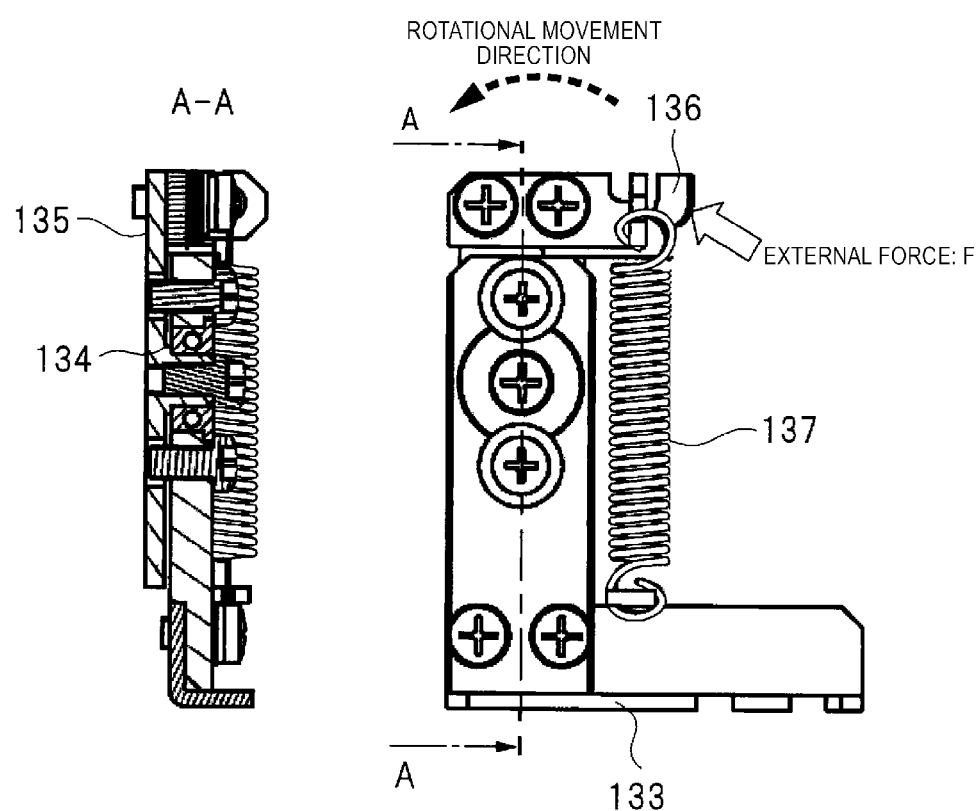

[Fig. 7]
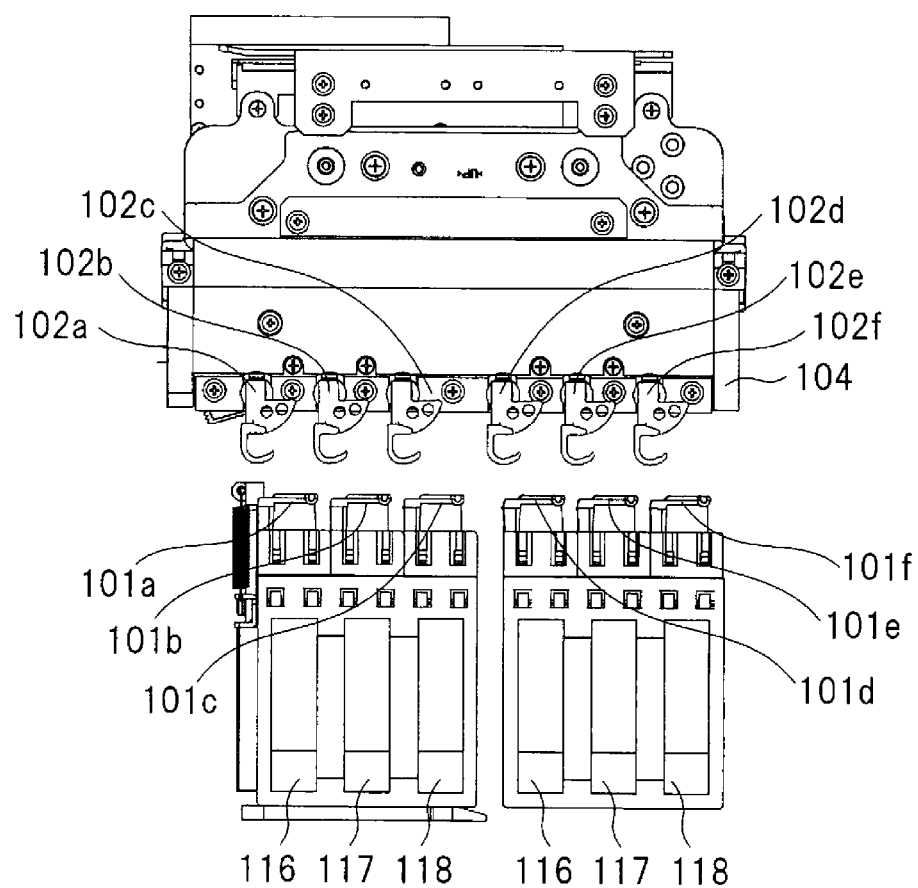

[Fig. 8]
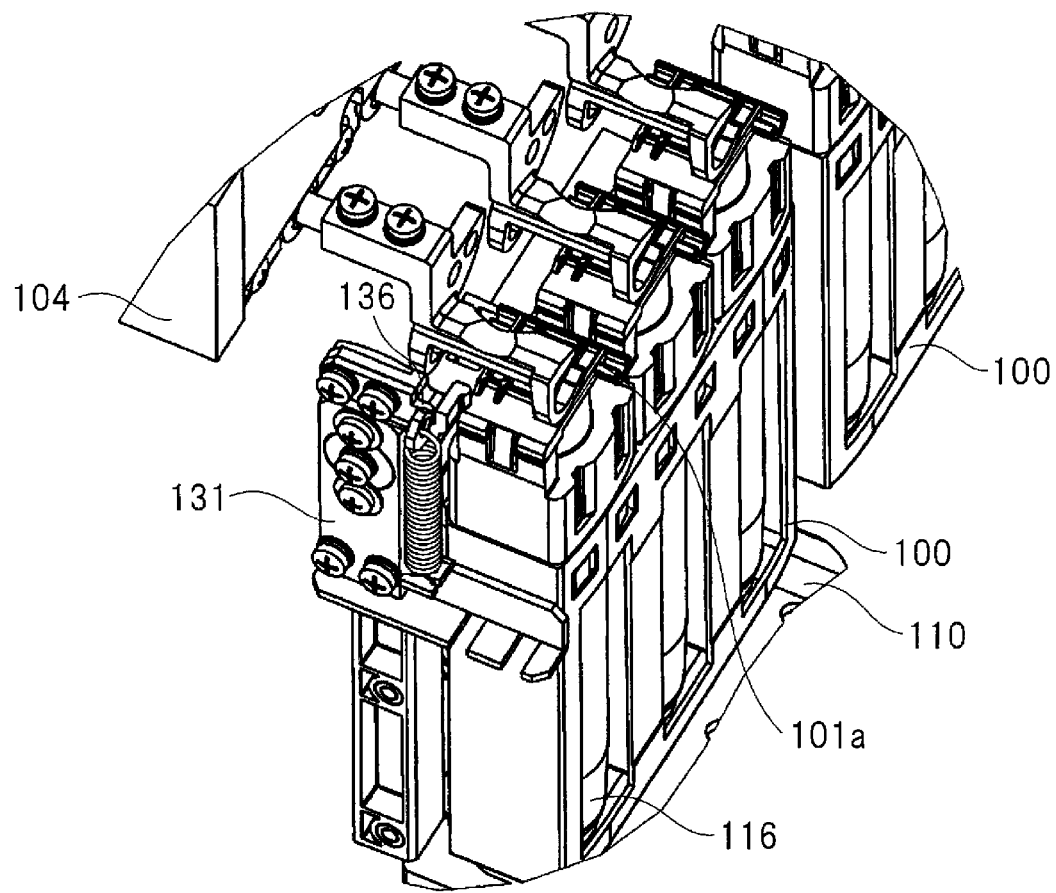

[Fig. 9]
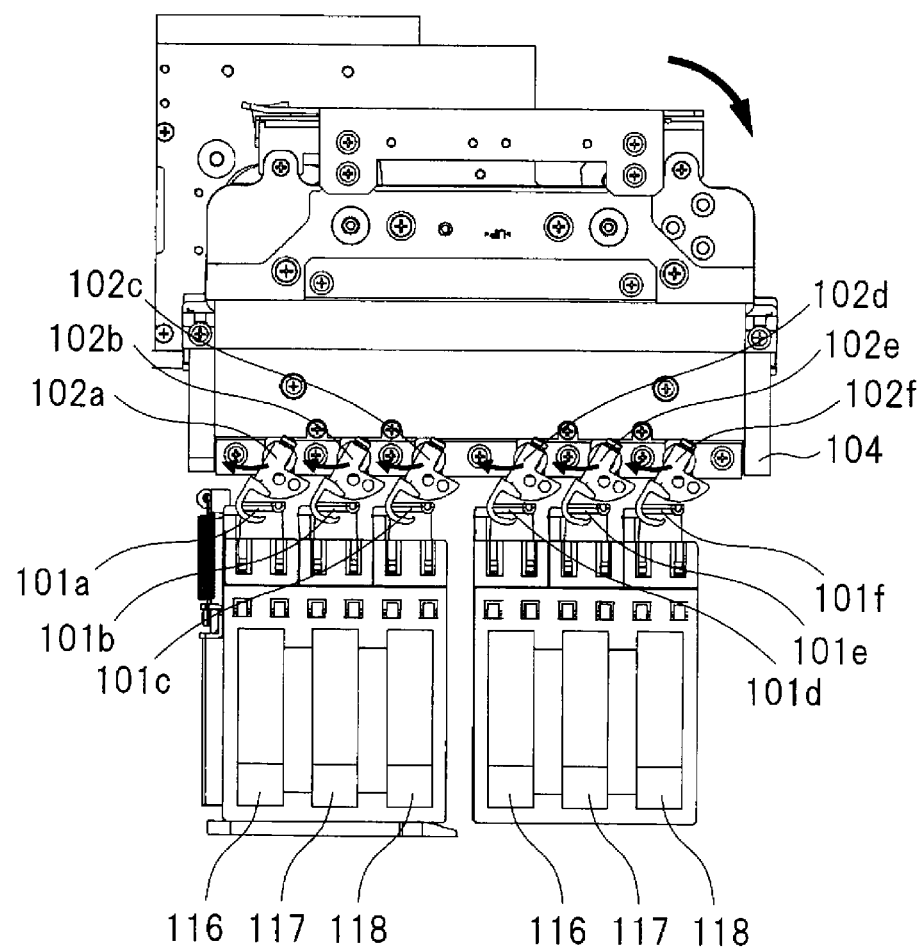

[Fig. 10]
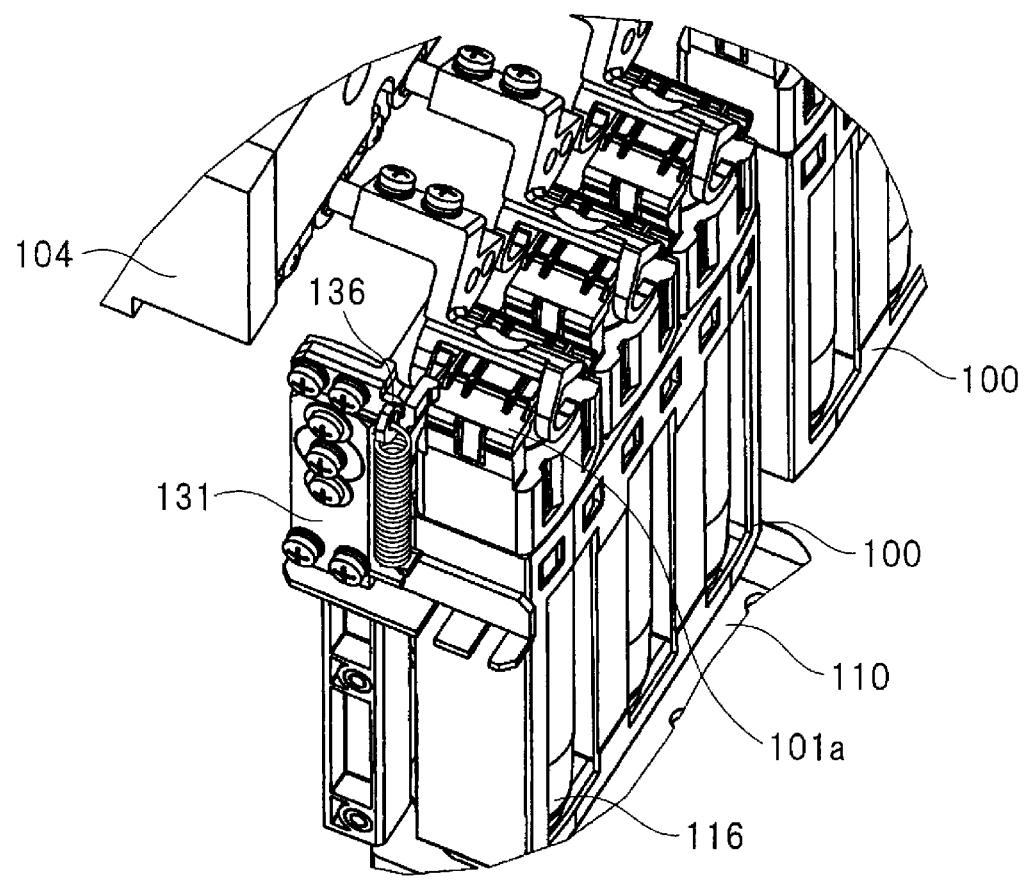

[Fig. 11]
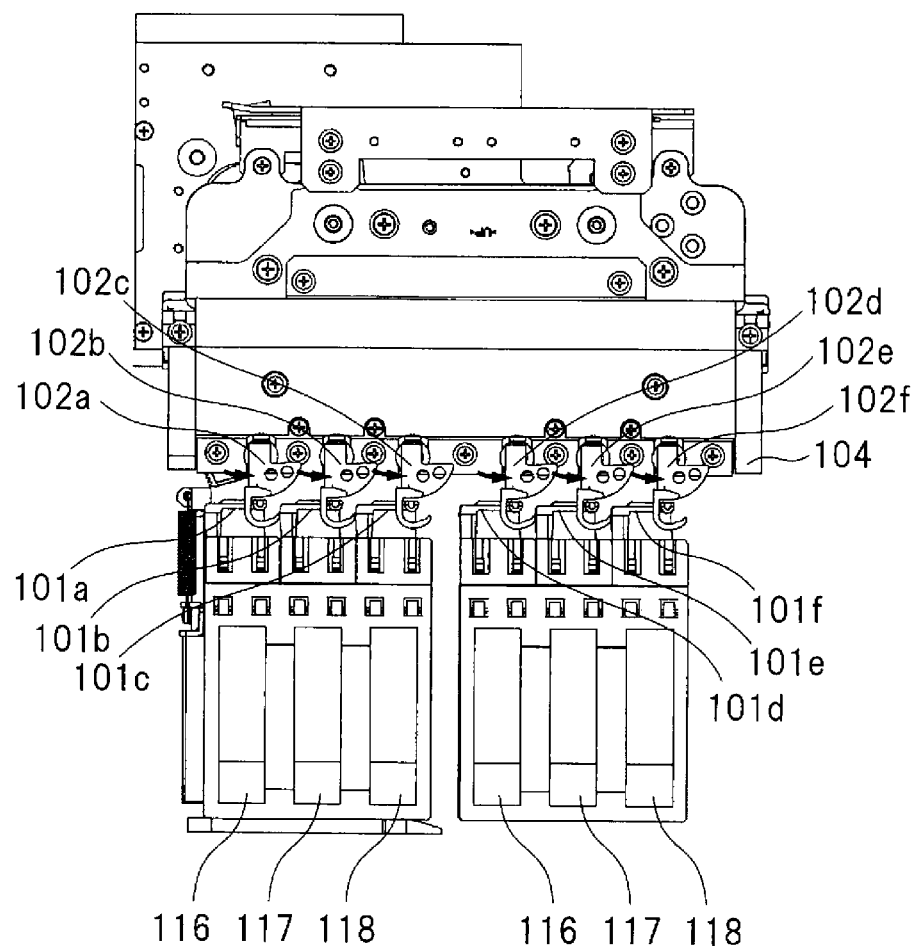

[Fig. 12]
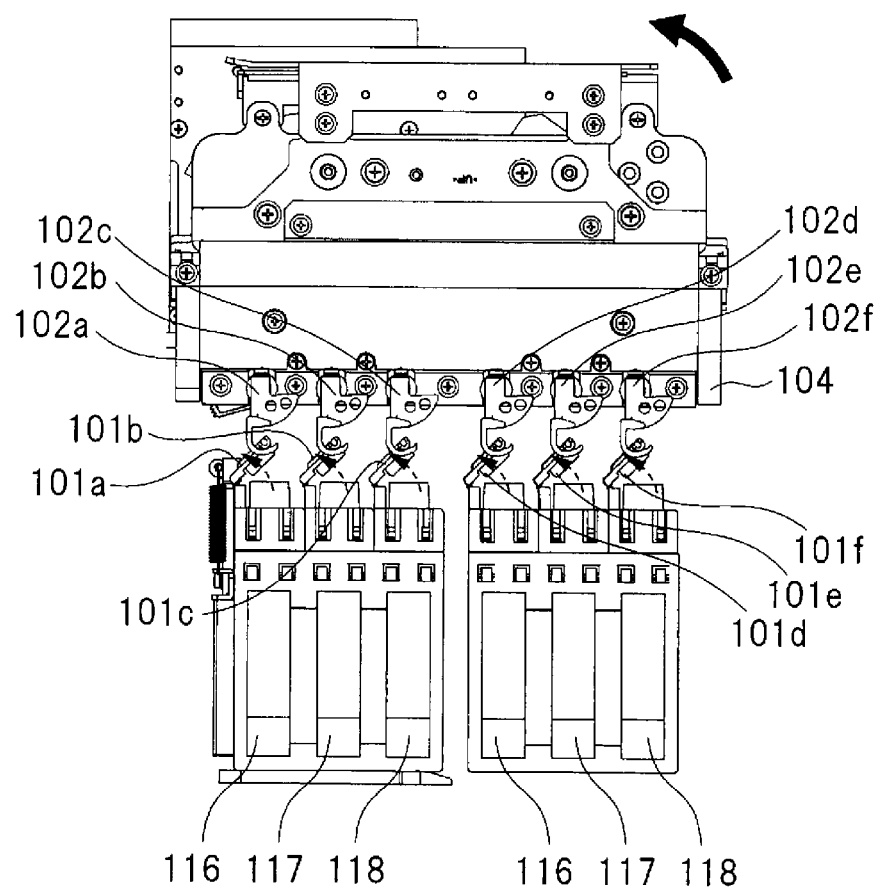

[Fig. 13]
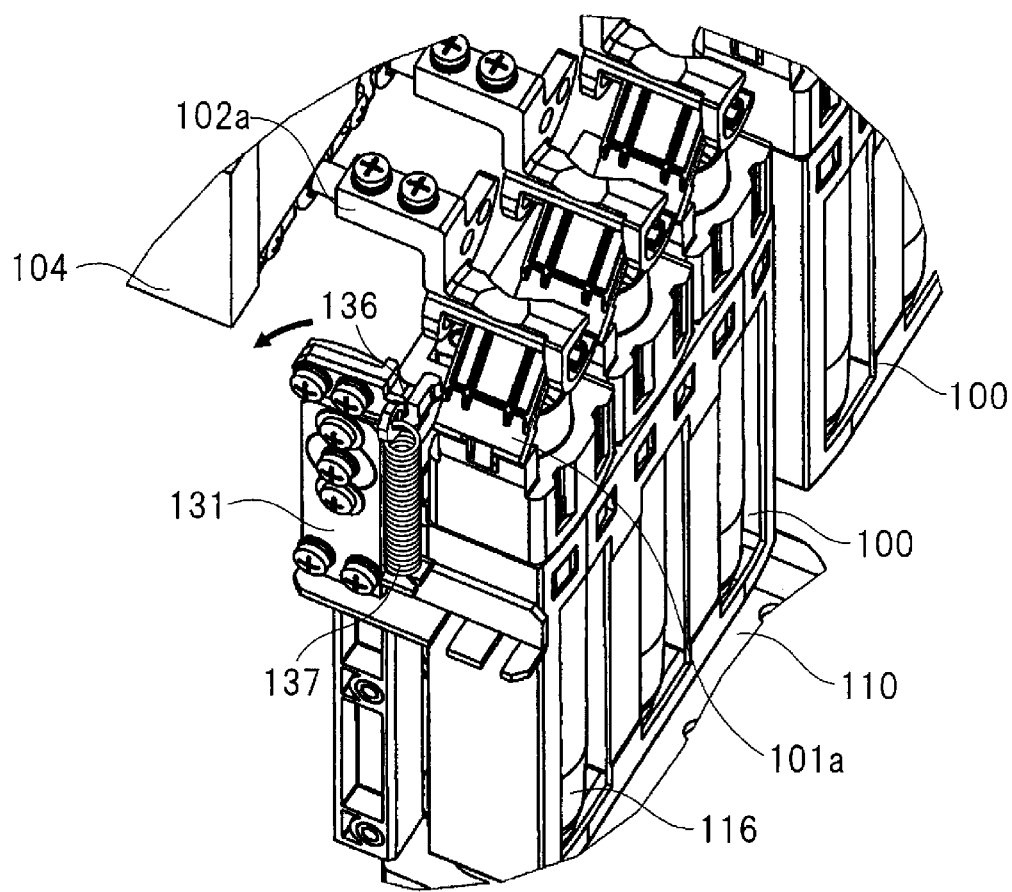

[Fig. 14]
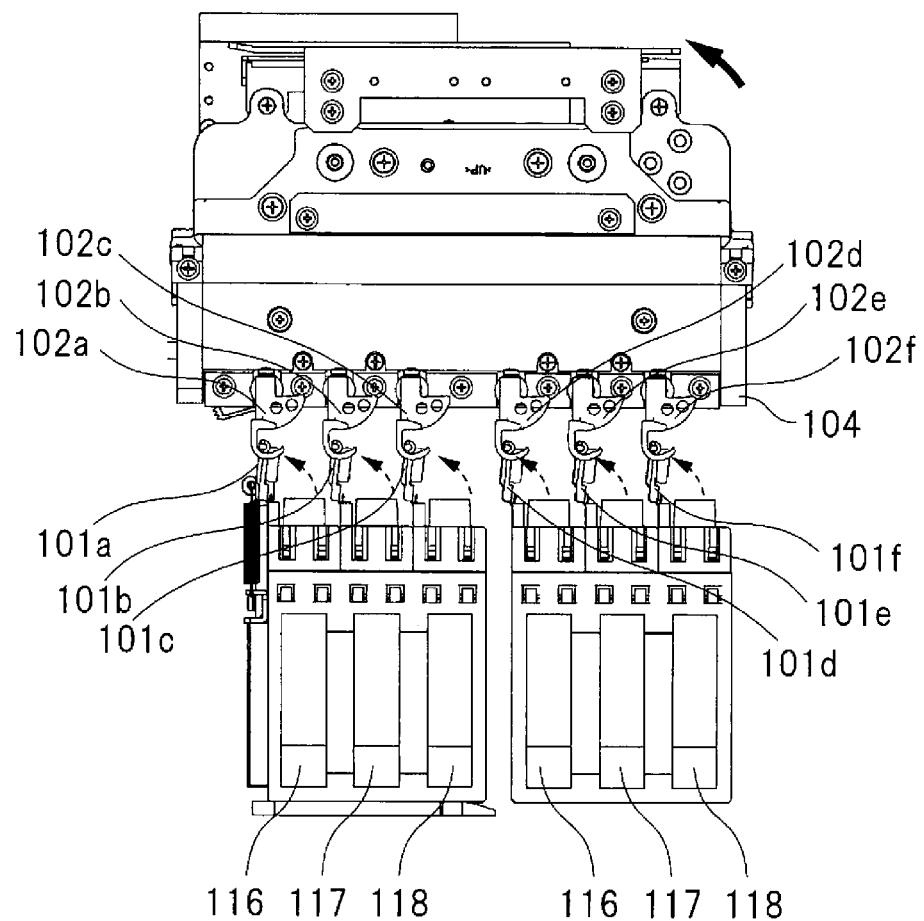

[Fig. 15]
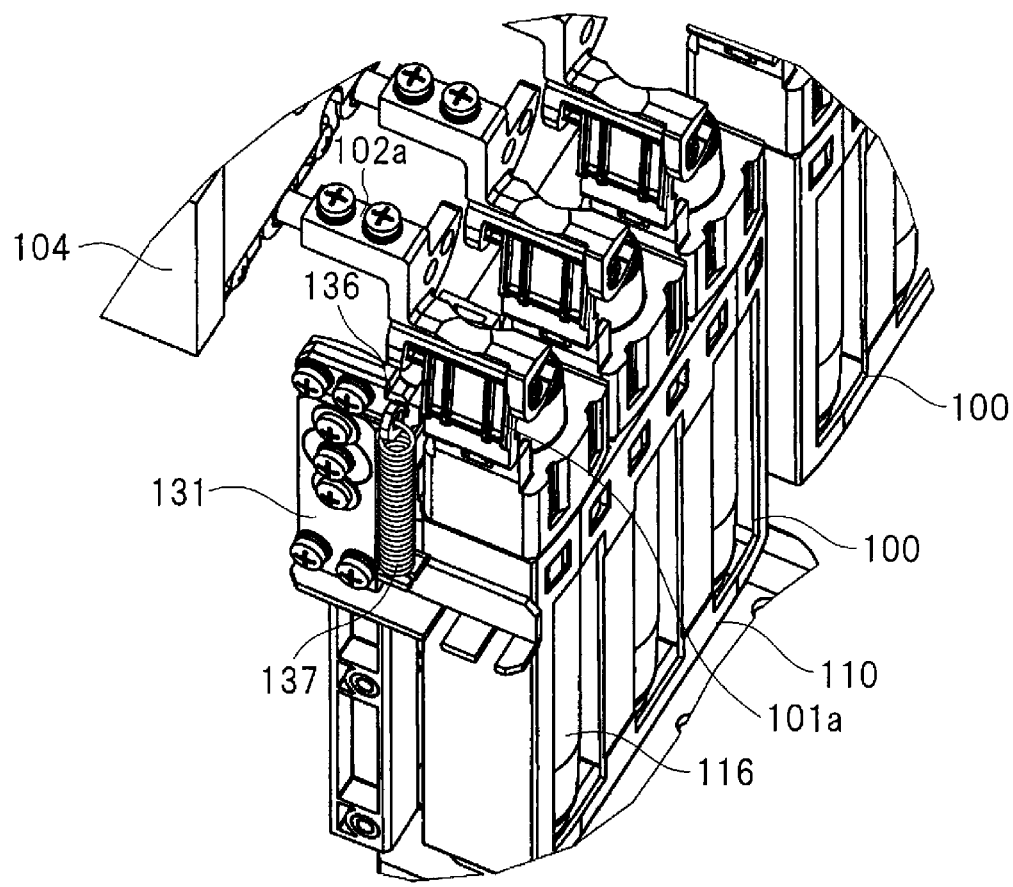

[Fig. 16]
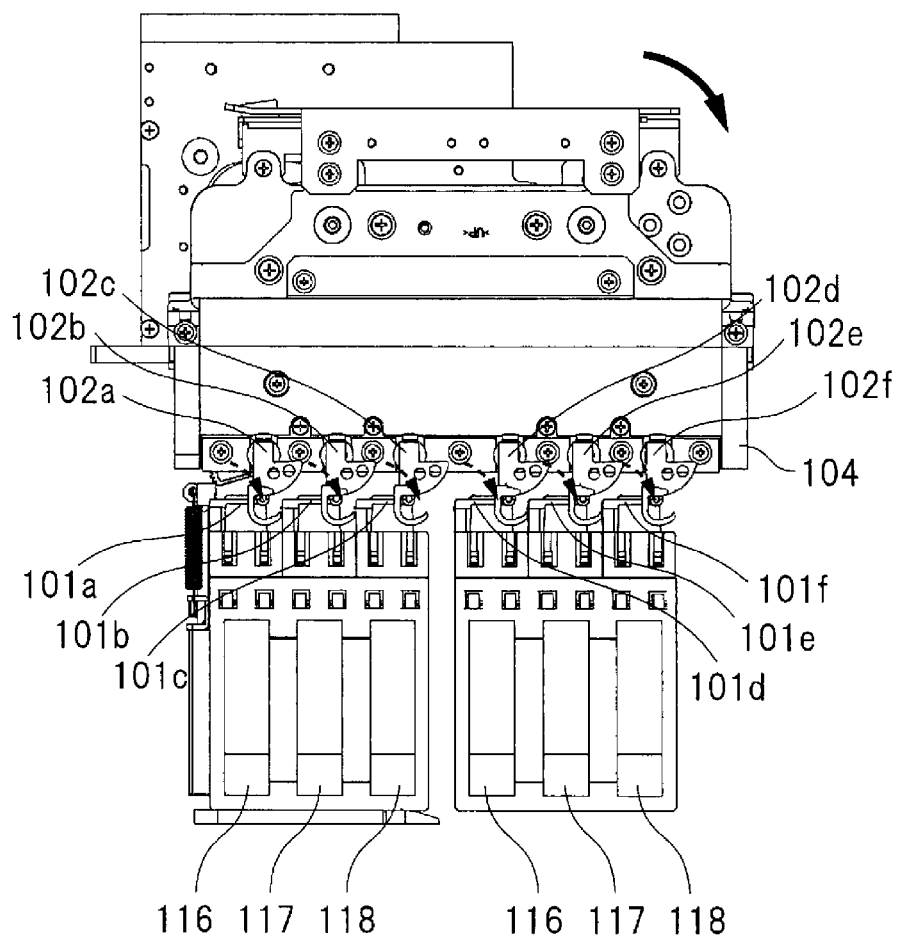

[Fig. 17]
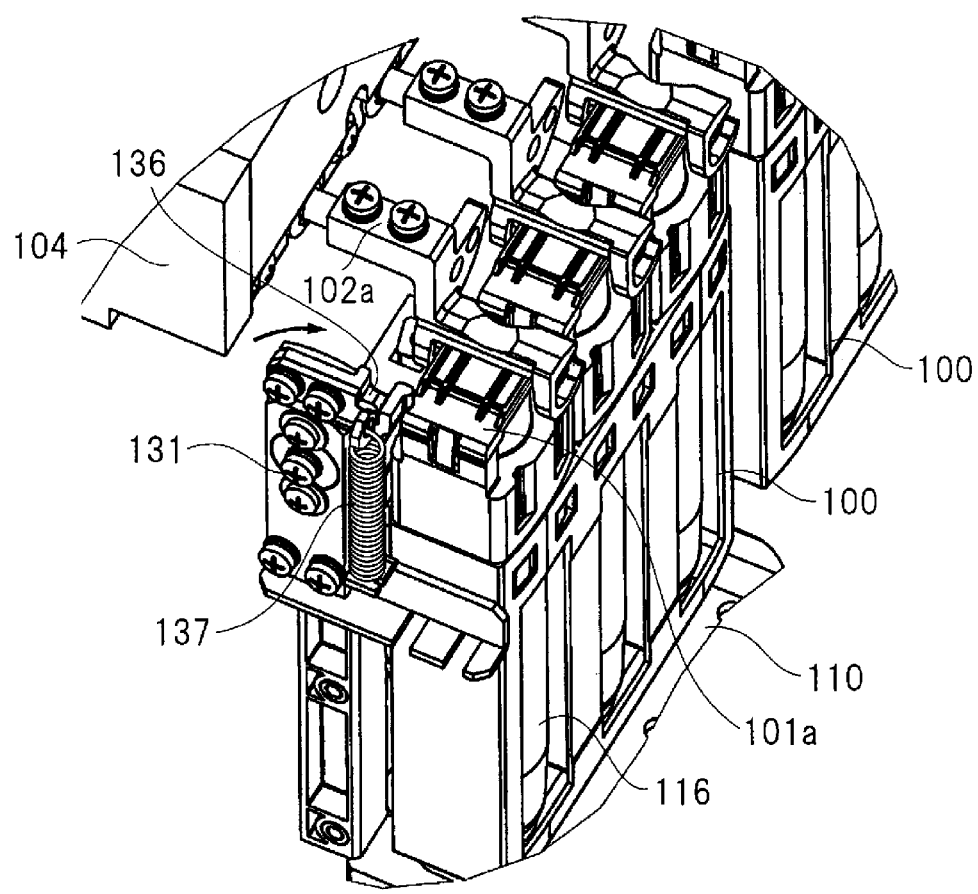

[Fig. 18]
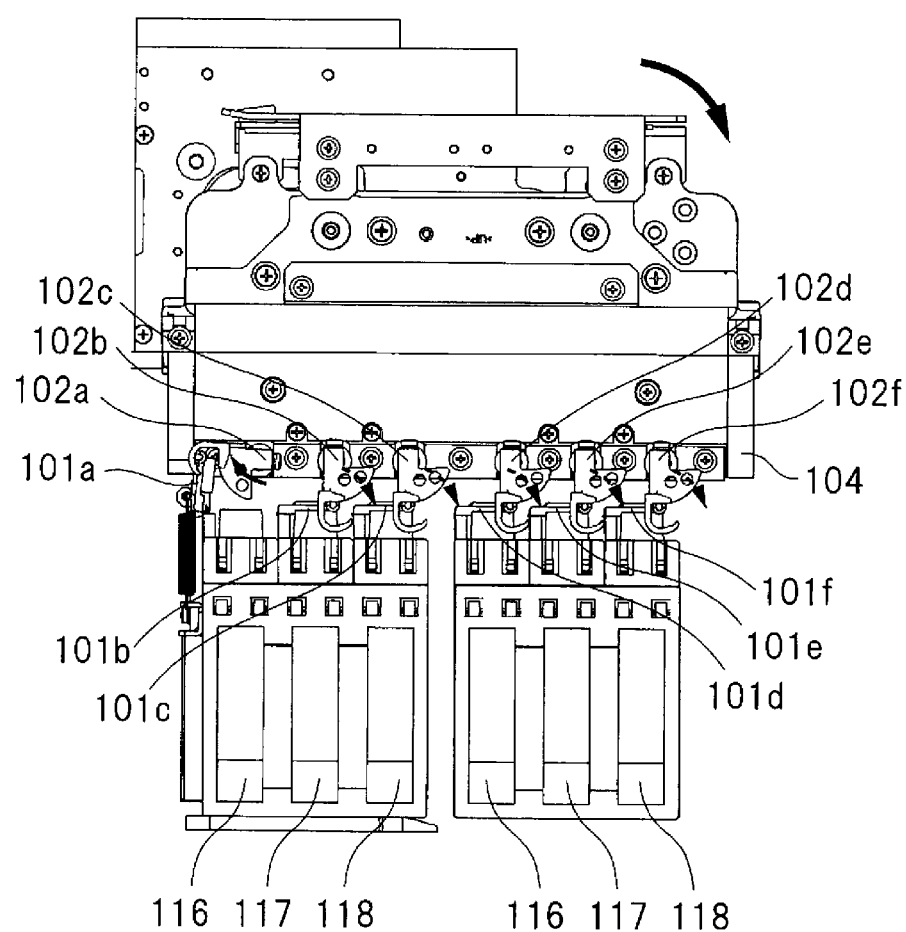

[Fig. 19]
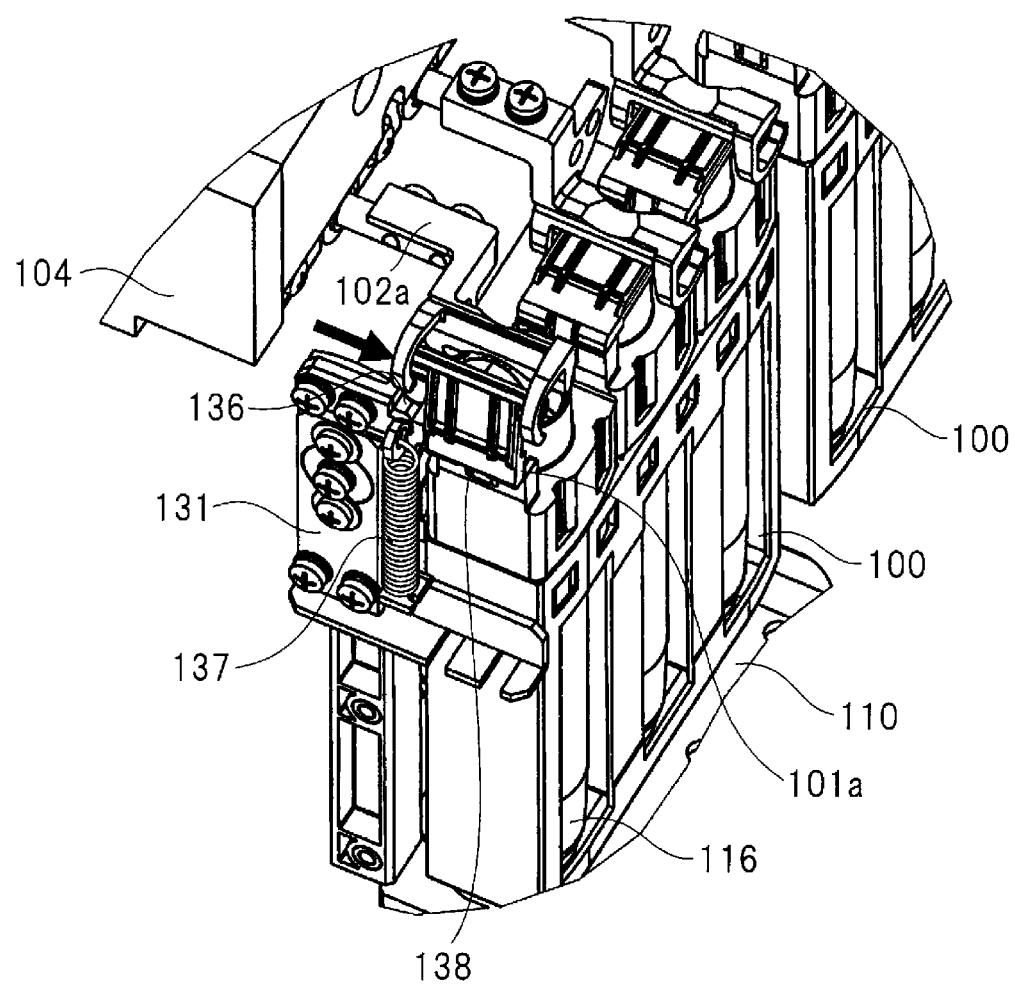

[Fig. 20]
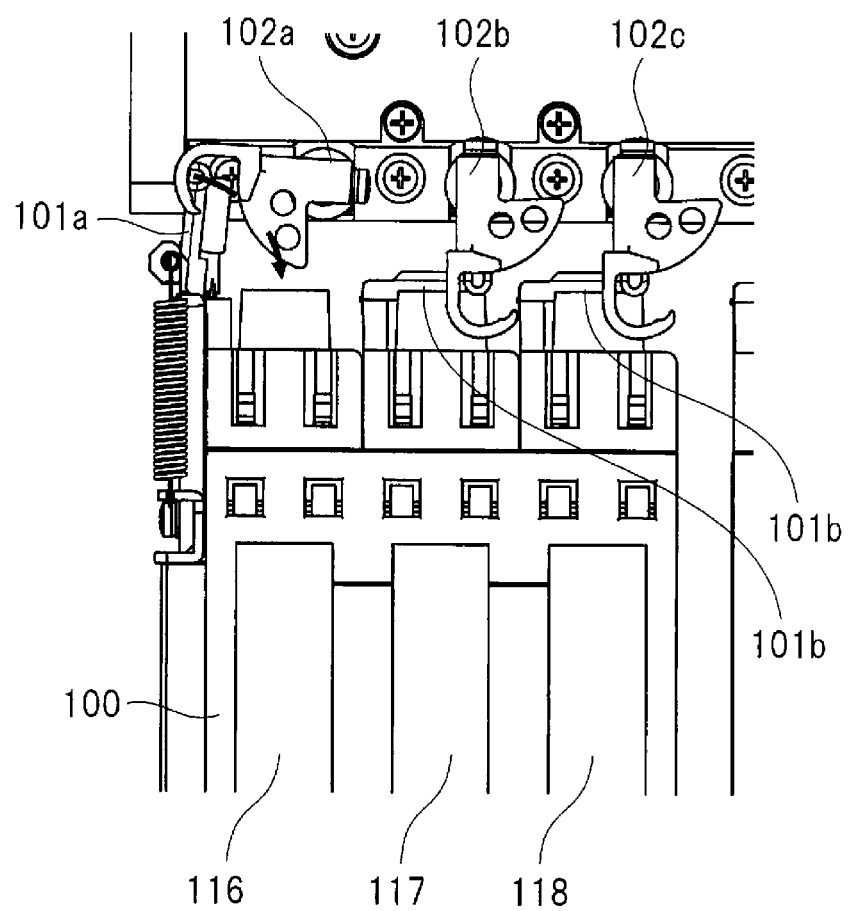

AUTOMATED ANALYZER

TECHNICAL FIELD

The present invention relates to an automated analyzer, and particularly to a technique useful for a stable operation of a container with a lid provided in the automated analyzer.

BACKGROUND ART

As a device performing chemical analysis such as biochemical analysis or immunological analysis in clinical examination, there is, for example, an automated analyzer.

In the automated analyzer, for example, in immunological analysis, magnetic particles, a labeled antibody containing a labeled substance, and an antibody binding the magnetic particles to a measurement target object are mixed with a sample containing the measurement target object so as to cause an antigen-antibody reaction.

A reaction product in which the measurement target object, the magnetic particles, and the labeled substance are bonded together is captured through magnetic separation, a voltage is applied to the captured reaction product so that a light emission amount thereof is measured, and thus the measurement target object is quantified.

In the automated analyzer, reaction reagents necessary for an analysis of a specimen sample are integrated into a single reagent cassette including a reagent container in which a solution containing magnetic particles is accommodated, a reagent container in which a solution containing a labeled substance is accommodated, and a reagent container in which a solution containing an antibody is accommodated for each an analysis item, and are prepared as a set for each a measurement item. The reagent containers are respectively attached with lids, and the lids are closed when the reagent containers are not used, and thus vaporization or deterioration of reagents are prevented.

Thus, a reagent container lid opening/closing mechanism opening and closing the lids of the reagent containers is required to be provided according to each piece of the analysis content. Opening and closing timings for reagents in the reagent containers provided in the region cassette are different from each other depending on the reaction process. Thus, the reagent container lid opening/closing mechanism is required to have a function of being capable of performing an opening/closing operation on each reagent container.

An automated analyzer may perform a plurality of analysis processes on one or more reagent containers in order to improve a throughput (refer to PTL 1). Thus, a reagent container lid opening/closing operation may include a case of performing opening/closing operations of lids of other reagent containers in a state in which lids of one or more reagent containers are opened.

CITATION LIST

Patent Literature

PTL 1: WO2011/074472

SUMMARY OF INVENTION

Technical Problem

The reagent container lid opening/closing mechanism disclosed in PTL 1 can selectively open and close lids of a plurality of reagent containers. Therefore, it is necessary to perform complex control in accordance with open/closed states of the lids of the plurality of reagent containers, and, thus, for example, there is a case of performing opening/closing operations of lids of other reagent containers in a state in which lids of one or more reagent containers are opened.

Specifically, the lid of the reagent container is rotationally moved with the fulcrum as the center, and is provided with a protrusion for being fitted to a functional part holding the lid in the reagent container lid opening/closing mechanism for the purpose of an opening/closing operation of the lid, and the reagent container lid opening/closing mechanism opens or closes the lid by holding the protrusion.

The lid of the reagent container is provided with an opening/closing spring supporting an opening/closing operation. The functional part holding the protrusion of the lid in the reagent container lid opening/closing mechanism has a hook shape such as a claw in a case of PTL 1, the hook is rotationally moved with respect to the rotation center located at a hook base part, so as to be fitted to the protrusion of the lid of the reagent container and to hold the protrusion, and thus an opening/closing operation of the lid can be performed.

However, in the device performing an opening/closing operation in the above technique, in a case of performing opening/closing operations of the lids of other reagent containers in a state in which the lids of one or more reagent containers are opened, a hook opening of the lid opening/closing mechanism overlaps a rotation trajectory of the lid of the reagent container with the fulcrum as the center. Therefore, there is concern that it may be difficult for the opening/closing mechanism to hold the protrusion of the lid of the reagent container.

In this case, the opening/closing spring is used to support an opening/closing operation of the lid of the reagent container, but a spring force becomes unstable over time with respect to even the opening/closing spring, and thus it cannot be said that sufficient supporting is possible. Thus, this causes the lid not to be held and thus the device to be stopped, and, as a result, there is concern that an analysis result may be delayed or a specimen sample may be lost.

An object of the present invention is to provide a technique of being capable of stably holding a lid of a reagent container in an open state without being influenced by an opening/closing operation of lids of other reagent containers.

The above and other objects and novel features of the present invention will become apparent from description of the present specification and the accompanying drawings.

Solution to Problem

A summary of a representative of the inventions disclosed in the present application will be described briefly as follows.

In other words, a representative automated analyzer includes a plurality of containers, a container holding device, a lid opening/closing mechanism, and a lid holding mechanism. The containers have lids rotationally moved centering on the fulcrum and store reagents. The container holding device is mounted with the plurality of containers. The lid opening/closing mechanism opens or closes the lids. The lid holding mechanism holds a lid opened by the lid opening/closing mechanism.

Particularly, the lid holding mechanism holds a lid of a container located at a dispensing/stirring position where dispensing and stirring of a reagent are performed.

Advantageous Effects of Invention

Effects achieved by the representative of the inventions disclosed in the present application will be described briefly as follows.

(1) It is possible to stabilize an analysis operation in an automated analyzer.

(2) It is possible to improve analysis performance on the basis of the above (1).

BRIEF DESCRIPTION OF DRAWINGS

FIG. 1 is an explanatory diagram illustrating an example of a configuration of an automated analyzer according to an embodiment.

FIG. 2 is a perspective view of a reagent refrigerator from which an upper cover is removed in the automated analyzer illustrated in FIG. 1.

FIG. 3 is a sectional view in which the reagent container from which the upper cover is removed in the automated analyzer illustrated in FIG. 1 is cut at a dispensing/stirring position.

FIG. 4 is a perspective view of a reagent container lid opening/closing mechanism provided in the automated analyzer illustrated in FIG. 1.

FIG. 5 is an explanatory diagram illustrating an example of an installation configuration of a lid holding mechanism provided in the automated analyzer illustrated in FIG. 1.

FIG. 6 is an explanatory diagram illustrating an example of a configuration of the lid holding mechanism illustrated in FIG. 5.

FIG. 7 is an explanatory diagram for explaining a specific operation sequence of lid opening and closing in reagent containers provided in an inner circumferential disk, reagent containers provided in an outer circumferential disk, and the reagent container lid opening/closing mechanism, which can be arranged at the dispensing/stirring position.

FIG. 8 is an explanatory diagram for explaining an operation and a function of the lid holding mechanism in the operation sequence illustrated in FIG. 7.

FIG. 9 is an explanatory diagram for explaining the operation sequence subsequent to FIG. 7.

FIG. 10 is an explanatory diagram for explaining an operation and a function of the lid holding mechanism in the operation sequence illustrated in FIG. 9.

FIG. 11 is an explanatory diagram for explaining the operation sequence subsequent to FIG. 9.

FIG. 12 is an explanatory diagram for explaining the operation sequence subsequent to FIG. 11.

FIG. 13 is an explanatory diagram for explaining an operation and a function of the lid holding mechanism in the operation sequence illustrated in FIG. 12.

FIG. 14 is an explanatory diagram for explaining the operation sequence subsequent to FIG. 12.

FIG. 15 is an explanatory diagram for explaining an operation and a function of the lid holding mechanism in the operation sequence illustrated in FIG. 14.

FIG. 16 is an explanatory diagram for explaining the operation sequence subsequent to FIG. 14.

FIG. 17 is an explanatory diagram for explaining an operation and a function of the lid holding mechanism in the operation sequence illustrated in FIG. 16.

FIG. 18 is an explanatory diagram for explaining the operation sequence subsequent to FIG. 16.

FIG. 19 is a perspective view of the periphery of the lid holding mechanism in an operation of closing remaining lids in a state of opening some lids by using hooks.

FIG. 20 is an enlarged view of detailed locations illustrated in FIG. 19.

DESCRIPTION OF EMBODIMENTS

In the following embodiment, for convenience, the embodiment will be described to be divided into a plurality of sections or embodiments as necessary, but, unless otherwise specified, they are not unrelated to each other, and one is in a relationship such as a modified example, details, and supplementary explanation of a part or the whole of the other.

In the following embodiment, in a case where the number of elements (including the number, a numerical value, an amount, a range, and the like) is mentioned, the number is not limited to the specific number unless otherwise specified and except for a case where the number is clearly limited to the specific number in principle, and may be the specific number or more.

In the following embodiment, a constituent element (also including an element step or the like) is, needless to say, not necessarily essential unless otherwise specified and except for a case where the constituent element is considered to be clearly essential in principle.

Similarly, in the following embodiment, a shape or a positional relationship of a constituent element or the like may include a shape or the like substantially approximate or similar to the shape or the like unless otherwise specified and except for a case where it is clearly not so in principle. This is also the same for the above numerical value and range.

The same member is given the same reference numeral in principle throughout all the drawings for explaining an embodiment, and repeated description thereof will be omitted.

Hereinafter, an embodiment will be described with reference to the drawings.

<Configuration Example of Automated Analyzer>

FIG. 1 is an explanatory diagram illustrating an example of a configuration of an automated analyzer 10 according to an embodiment.

The automated analyzer 10 automatically performs chemical analysis such as biochemical analysis or immunological analysis in clinical examination. Here, a description will be made of an automated analyzer using a magnetic particle reagent for sample analysis as an example, but the kind of reagent or the like is not particularly limited.

As illustrated in FIG. 1, the automated analyzer 10 is formed of a magnetic separation stirring device 11, a reagent refrigerator 115, a reagent container lid opening/closing mechanism 121, an incubator 12, a reagent dispensing mechanism 13, a reaction detection unit 14, a shipper 15, a specimen dispensing nozzle 16, a reaction container 17, a specimen dispensing tip 18, a gripper 19, a transport mechanism 20, and a reagent stirring mechanism 21.

The transfer shipper 15 transfers a reaction liquid from the incubator 12 to the reaction detection unit 14. The gripper 19 transfers the reaction container 17 from the incubator 12 to the magnetic separation stirring device 11. The transport mechanism 20 transports the reaction container 17 and the specimen dispensing tip 18.

Next, a fundamental operation of the automated analyzer 10 will be described.

First, the reaction container 17 disposed in a container holder 22 is disposed on the incubator 12 by the transport mechanism 20. A specimen is put in a specimen container 23 such as a test tube, and is placed on a specimen transport rack 24 so as to be moved to a specimen suction location. The specimen dispensing tip 18 disposed in a specimen dispensing tip holder 25 is moved to a tip attachment location 26 by the transport mechanism 20.

Here, the specimen dispensing tip 18 is attached to a tip end of the specimen dispensing nozzle 16, a specimen is sucked by the specimen dispensing nozzle 16 attached with the specimen dispensing tip 18, and is ejected onto the reaction container 17 on the incubator 12 at a specimen dispensing location 27.

After the specimen is dispensed, the specimen dispensing tip 18 is discarded into a discarding box (not illustrated). A plurality of reagent containers 116 to 118 are disposed in the reagent refrigerator 115. An upper open part of the reagent refrigerator 115 and the reagent container lid opening/closing mechanism 121 are covered with an upper cover 115a which is partially illustrated, and thus it is possible to improve cold insulation efficiency through thermal insulation and to prevent permeation of dust or contaminant.

The reagent dispensing mechanism 13 can be moved in parallel in a horizontal direction, immerses a tip end of a reagent suction probe 108 illustrated in FIG. 4 into a reagent in a predetermined reagent containers 116 to 118 through an opening formed in the upper cover 115a, and sucks a predetermined amount of reagent.

Next, the reagent dispensing mechanism 13 is moved up so as to be moved in parallel to a predetermined position over the incubator 12, and ejects the reagent into the reaction container 17. The reagent stirring mechanism 21 can also be moved in parallel in the horizontal direction, immerses a tip end of a reagent stirring rod 109 illustrated in FIG. 4 into a reagent in a predetermined reagent containers 116 to 118 through an opening formed in the upper cover 115a, and stirs the specimen.

After a reaction occurs on the incubator 12 for a predetermined period of time, the reaction container 17 is moved to the magnetic separation stirring device 11 by the gripper 19. After a reaction liquid is subject to magnetic separation in the magnetic separation stirring device 11, or cleaning is performed by a nozzle part 28, the reaction container 17 is transferred again to the incubator 12 from the magnetic separation stirring device 11 by the gripper 19.

After a reaction occurs on the incubator 12 for a predetermined period of time, a reaction liquid is transferred to the reaction detection unit 14 by the shipper 15, and a signal is detected from the reaction liquid. The shipper 15 sucks not only a reaction liquid but also a buffer solution and a detection channel cleaning solution according to predefined operation instructions.

<Analysis Operation Example>

FIG. 2 is a perspective view of the reagent refrigerator 115 from which the upper cover 115a is removed in the automated analyzer 10 illustrated in FIG. 1, and FIG. 3 is a sectional view in which the reagent refrigerator 115 from which the upper cover 115a is removed in the automated analyzer 10 illustrated in FIG. 1 is cut at a dispensing/stirring position 113.

The reagent refrigerator 115 includes a reagent disk 120 and the reagent container lid opening/closing mechanism 121.

The reagent disk 120 can be mounted with a plurality of sets of cassettes 100 illustrated in FIG. 4. Each of the cassettes 100 which are container holding devices accommodates three reagent containers 116 to 118 storing a reagent used for analysis of a sample as one set. The reagent container lid opening/closing mechanism 121 which is a lid opening/closing mechanism opens and closes lids 101 of the reagent containers 116 to 118 of the cassette 100 located at the dispensing/stirring position 113 over the reagent disk 120.

The cassettes 100 are disposed radially on the reagent disk 120. The reagent disk 120 is provided with an outer circumferential disk 110 and an inner circumferential disk 111, and only the outer circumferential disk 110 is rotated horizontally around a vertical axis.

The inner circumferential disk 111 is fixed, and has the dispensing/stirring position 113 at which a reagent is dispensed and stirred. The cassettes 100 can be moved between the inner circumferential disk 111 and the outer circumferential disk 110 by a reagent container inner/outer circumference movement portion (not illustrated) in order to perform an analysis process.

A frame 114 is provided to cross over the outer circumferential disk 110 and the inner circumferential disk 111 in the reagent disk 120, and the reagent container lid opening/closing mechanism 121 is fixed to the frame 114 and is disposed over the dispensing/stirring position 113.

In a case where an analysis process is performed in the automated analyzer 10, for example, if a magnetic particle reagent is accommodated in the reagent container 116, and different reagents A and B are respectively accommodated in the reagent containers 117 and 118, and the three kinds of reagents are treated as a set in the cassette 100, first, at least one of the reagents A and B is mixed with a specimen, that is, a sample so as to be heated for a predetermined period of time so that a reaction is caused to progress.

Thereafter, either one of the reagents A and B is mixed with the magnetic particle reagent so as to be further heated for a predetermined period of time so that a reaction is caused to progress. In the automated analyzer 10, a reaction liquid generated in the above-described way is analyzed by an analysis portion (not illustrated) in the subsequent stage.

However, dilution of a specimen, a cleaning process before analysis, or the like may be performed in a case where a mixing order of each reagent or heating time is changed depending on an analysis item, or as necessary. The reagent suction probe 108 illustrated in FIG. 4 and the reagent stirring rod 109 illustrated in FIG. 4 respectively dispensing and stirring a reagent can simultaneously access the target reagent containers 116 to 118 set in each cassette 100 on the outer circumferential disk 110 and the inner circumferential disk 111.

The outer circumferential disk 110 side of the dispensing/stirring position 113 is a position at which the reagent suction probe 108 accesses a target container among the reagent containers 116 to 118 located at this position so that a reagent is dispensed. The inner circumferential disk 111 side of the dispensing/stirring position 113 is a position at which the magnetic particle reagent in the reagent container 116 located at this position is stirred with the reagent stirring rod 109.

A reagent to be used is fundamentally stirred in the following cycle at the dispensing/stirring position 113. In other words, when the current analysis cycle transitions to the next analysis cycle, the cassette 100 in which a magnetic reagent stirring process is completed is moved from the upper side 112 of the inner circumferential disk 111 to the upper side of the outer circumferential disk 110 by reagent container inner/outer circumference movement means (not illustrated), and a stirred magnetic particle reagent is dispensed thereinto at the next analysis cycle.

However, reagents may be dispensed from the reagent containers 116 to 118 on the inner circumferential disk 111, for example, in a case of an emergency process or depending on an analysis item.

<Configuration Example and Operation of Reagent Container Lid Opening/Closing Mechanism>

FIG. 4 is a perspective view of the reagent container lid opening/closing mechanism 121 of the automated analyzer 10 illustrated in FIG. 1.

The reagent container lid opening/closing mechanism 121 includes a unit base 107, a hook part 104, a lid opening/closing drive device 106, and a plurality of hooks 102. The unit base 107 is fixed to the frame 114. The hook part 104 is connected to the unit base 107.

The lid opening/closing drive device 106 moves the hook part 104 in parallel in an opening/closing direction of the lids 101 of the reagent containers 116 to 118 with respect to the unit base 107. The plurality of hooks 102 are provided in the hook part 104.

Although not particularly illustrated, the hook part 104 is provided with a plurality of hook drive devices which individually rotationally move the respective hooks 102 with respect to the hook part 104 so as to engage and disengage corresponding hooks with and from the lids 101 of the reagent containers 116 to 118.

Here, a set of the reagent containers 116 to 118 are set in a single cassette 100, and three kinds of reagents are held in a single cassette 100 if different reagents are respectively put in the reagent containers.

In the present embodiment, two sets of the reagent containers 116 to 118 are arranged at the dispensing/stirring position 113 in a diameter direction of the reagent disk 120. In the present embodiment, two sets each including the three reagent containers 116 to 118 are disposed side by side at the dispensing/stirring position 113, but the number of sets may be increased depending on a size of the reagent disk 120. There may be a configuration in which only one set of the reagent containers 116 to 118 is disposed at the dispensing/stirring position 113, or there may be a configuration in which three or more sets thereof can be disposed thereat.

A description has been made of an example of a case where three reagent containers 116 to 118 are mounted in a single cassette 100, but two reagent containers or four or more reagent containers may be set in the cassette 100 depending on the reagent disk 120 or the cassette 100.

The present invention is not limited to a configuration in which a plurality of reagent containers form a set in a single cassette 100, and there may be a configuration in which a single reagent container not forming a set with other reagent containers is separately set at the dispensing/stirring position 113.

The unit base 107 is fixed to the front frame 114 with bolts or the like, and has a fixed positional relationship with respect to the reagent disk 120. In the example illustrated in FIG. 4, the lid opening/closing drive device 106 is fixed to the unit base 107 via a bracket or the like as appropriate.

A motor, a cylinder, or the like may be used in the lid opening/closing drive device 106, and, for example, a pulse motor is used. The hook part 104 is linked to the lid opening/closing drive device 106 via a parallel link formed of two arms 105, and is moved in parallel in an opening/closing direction of the lids 101 of the reagent containers 116 to 118 if the arms 105 are rotationally moved due to an operation of the lid opening/closing drive device 106.

In a case of the present embodiment, an opening/closing operation of the lid 101 corresponds to arc movement, and thus the hook part 104 also draws an arc trajectory so as to be moved in parallel. The hooks 102 are claw components for hooking the lids 101 of the reagent containers 116 to 118, and six hooks are provided under the hook part 104 along the diameter direction of the reagent disk 120 in accordance with the number of reagent containers 116 to 118 which can be arranged at the dispensing/stirring position 113.

Of course, the number of hooks 102 may be changed by design depending on the number of reagent containers 116 to 118 which can be arranged at the dispensing/stirring position 113. The number of hooks 102 is not the same as the number of reagent containers 116 to 118 which can be arranged at the dispensing/stirring position 113, and the lids 101 of a plurality of reagent containers 116 to 118 which are opening/closing targets may be selectively opened and closed with a single or a plurality of hooks.

In this case, an opening/closing hook movement mechanism (not illustrated) for moving the hooks 102 to the lids 101 of the reagent containers 116 to 118 which are opening/closing targets is provided between the frame 114 and the reagent container lid opening/closing mechanism 121, or is additionally provided in the reagent container lid opening/closing mechanism 121.

Each of the hooks 102 is linked to an output shaft of a corresponding hook drive device (not illustrated) in the hook part 104 via a hook shaft 103, and is rotationally moved and displaced centering on the hook shaft 103 due to an operation of the hook drive device. A motor, a cylinder, or the like may be used in the hook drive device, and, here, for example, a pulse motor is assumed to be used.

Next, a description will be made of an operation of the reagent container lid opening/closing mechanism 121.

In summary, the reagent container lid opening/closing mechanism 121 selectively engages the corresponding hook 102 with the lid 101 of a container desired to be opened or closed among the six reagent containers 116 to 118 located at the dispensing/stirring position 113. The reagent container lid opening/closing mechanism 121 displaces the hook part 104 in an opening direction or a closing direction in this state so as to open or close only the lid 101 engaged with the hook 102.

For example, in a case of opening the lid 101 of a specific reagent container, the corresponding hook 102 is lowered to an engagement position in a state in which the hook part 104 is located at a lower position, that is, a position where the hook part has fallen in the closing direction. Here, the lid 101 of the specific reagent container is assumed to the lid of the reagent container 117 on the inner circumferential disk 111.

The hook part 104 is displaced to an upper position, that is, a position where the hook part has risen in the opening direction by driving the lid opening/closing drive device 106, and thus only the lid 101 of the reagent container 117 hooked by the hook 102 is pulled up.

Conversely, in a case where the lid 101 of the reagent container 117 is closed, the lid opening/closing drive device 106 is driven in a state in which the corresponding hook 102 is lowered to the engagement position so that the hook part 104 is displaced from the upper position in the closing direction, and thus the lid 101 of the reagent container 117 is pressed down with the hook 102.

In other words, when the lid 101 of the reagent container 117 is opened, and then is closed in the next operation, the hook part 104 may be displaced in the closing direction from the posture after the opening operation so as to be moved to the lower position.

<Installation Example of Lid Holding Mechanism>

FIG. 5 is an explanatory diagram illustrating an example of an installation configuration of a lid holding mechanism 131 provided in the automated analyzer 10 illustrated in FIG. 1. FIG. 5(*a*) is a perspective view of the lid holding mechanism 131 attached to an inner circumferential disk base 132, FIG. 5(*b*) is a top view thereof, and FIG. 5(*c*) is a side view thereof.

The lid holding mechanism 131 illustrated in FIG. 5 is provided in the inner circumferential disk 111, and is fixed to the inner circumferential disk base 132 attached with the inner circumferential disk 111 via bolts or the like. As will be described later, the lid holding mechanism 131 has a function of holding a lid 101*a* of the reagent container 116.

In a case of being viewed from the surface, a pressing force for lid holding acts vertically in a longitudinal direction of the cassette 100. Of course, the lid holding mechanism 131 may be provided in the outer circumferential disk 110 illustrated in FIG. 4 in addition to the inner circumferential disk 111. The lid holding mechanism 131 is not limited to the lid 101*a*, and the number thereof may be changed by design depending on the number of reagent containers 116 to 118 and an application of an opening/closing operation.

In the present embodiment, the lid holding mechanism 131 is provided such that a pressing force for lid holding acts vertically in the longitudinal direction of the cassette 100. This is so that an operation of the reagent container lid opening/closing mechanism 121 illustrated in FIG. 4 is not influenced. The lid holding mechanism 131 may be provided at any location as long as the location does not influence an operation of the reagent container lid opening/closing mechanism 121 illustrated in FIG. 4, and a pressing force for lid holding acts.

<Configuration Example of Lid Holding Mechanism>

Next, a description will be made of a configuration of the lid holding mechanism 131 with reference to FIG. 6.

FIG. 6 is an explanatory diagram illustrating an example of a configuration of the lid holding mechanism 131 illustrated in FIG. 5. FIG. 6(*a*) is a perspective view of the lid holding mechanism 131, FIG. 6(*b*) is a side view of the lid holding mechanism 131, and FIG. 6(*c*) is a sectional view taken along A-A in FIG. 6(*b*).

The lid holding mechanism 131 includes a holding mechanism base portion 133, a bearing 134, a holding drive part 135, a protrusion member 136, and an elastic member 137. In the lid holding mechanism 131, the holding mechanism base portion 133 is fixed to the inner circumferential disk base 132 illustrated in FIG. 5 via bolts or the like.

The holding drive part 135 which is rotated via the bearing 134 serving as a support pin is provided at the holding mechanism base portion 133. The protrusion member 136 which is a protrusion is provided at a front end of the holding drive part 135, and the elastic member 137 is provided between the protrusion member 136 and the holding mechanism base portion 133.

One end of the elastic member 137 is connected to the holding mechanism base portion 133, and the other end of the elastic member 137 is connected to the protrusion member 136. These elements form a structure having a rotation link mechanism for not hindering an opening/closing operation of a lid of a reagent container.

The protrusion member 136 comes into contact with the lid 101*a* in FIG. 5 so as to maintain an open state of the lid from the vertical direction with respect to the rotational movement direction of the lid 101*a* of the reagent container 116 in FIG. 5 rotationally moved centering on the fulcrum.

The elastic member 137 generates a pressing force for generating friction between the lid 101*a* and the protrusion member 136 in order to hold the lid 101*a*.

In other words, the elastic member 137 generates the pressing force in a direction opposite to the rotational movement direction of the protrusion member 136 when the lid 101*a* is opened or closed. In a case where the lid 101*a* is opened, the pressing force is generated in a direction opposite to the rotational movement direction indicated by a turning arrow in FIG. 6(*b*).

Consequently, the protrusion member 136 is moved between the lid 101*a* and the reagent container 116 in FIG. 5, that is, to an opening position, and thus an open state of the lid 101*a* is maintained.

In FIG. 6, the tension coil spring is used as the elastic member 137 as an example, but the elastic member 137 is not limited thereto, and, for example, an elastically deformed member such as a rubber, a gas damper, or oil may be used.

Thus, if the protrusion member 136 receives external force F from an arrow direction illustrated in FIG. 6, the holding drive part 135 is rotationally moved in the counterclockwise direction centering on the bearing 134. In the middle of being rotationally moved in the counterclockwise direction, the pressing force as force resisting against the external force is generated at the surface of the protrusion member 136 receiving the external force due to an attractive force of the elastic member 137. If the external force disappears, the protrusion member 136 is rotationally moved in the clockwise direction due to the attractive force of the elastic member 137, and is thus returned to the state illustrated in FIG. 6(*a*).

<Specific Operation Examples of Reagent Container Lid Opening/Closing Mechanism and Lid Holding Mechanism>

Next, a description will be made of a specific operation sequence of lid opening and closing performed by the reagent container lid opening/closing mechanism 121 and the lid holding mechanism 131 with reference to FIGS. 7 to 19.

FIGS. 7, 9, 11, 12, 14, 16 and 18 are explanatory diagrams for explaining a specific operation sequence of lid opening and closing related to the reagent containers 116 to 118 which can be arranged at the dispensing/stirring position 113 and provided in the inner circumferential disk 111, the reagent containers 116 to 118 provided in the outer circumferential disk 110, and the reagent container lid opening/closing mechanism 121. FIGS. 8, 10, 13, 15, 17 and 19 are explanatory diagrams for explaining an operation and a function of the lid holding mechanism 131 in this operation sequence.

In FIGS. 7, 9, 11, 12, 14, 16 and 18, for convenience of description, the letters a to f are added to the hooks 102 and the lids 101 in order from the left. An operation of the hook part 104 is indicated by a solid thick arrow, an operation of the hook 102 is indicated by a thin solid arrow, and operations of the lids 101 of the reagent containers 116 to 118 are indicated by dotted arrows.

First, FIG. 7 illustrates a state in which the hook part 104 is located at a reference position, the lids 101*a* to 101*f* of the reagent containers 116 to 118 are all closed, the hook part 104 is stopped at the upper position, and the hooks 102*a* to 102*f* are oriented vertically downward.

In this case, as illustrated in FIG. 8, the cassette 100 is drawn into the inner circumferential disk 111 by a reagent container inner/outer circumference movement portion (not illustrated), but the lid holding mechanism 131 is disposed not to hinder a movement operation of the cassette 100. Particularly, the protrusion member 136 is located not to contact with the lid 101a of the reagent container 116. Thus, at this point, the lid holding mechanism 131 does not perform a rotational movement operation.

FIG. 9 illustrates a state right before the hooks 102a to 102f are hooked to the lids 101a to 101f of the reagent containers 116 to 118.

In FIG. 9, the hook part 104 is moved from the upper position to the lower position in the state illustrated in FIG. 7 due to operations of the arms 105 in FIG. 4, and the hooks 102a to 102f are rotationally moved and displaced in the clockwise direction in the figure by a predetermined angle so as not to contact with the corresponding lids 101a to 101f. Here, the clockwise direction in the figure will also be hereinafter referred to as a separation direction.

In this case, as illustrated in FIG. 10, the hooks 102a to 102f are rotationally moved and displaced in the separation direction by the predetermined angle, and the hook part 104 is moved from the upper position to the lower position, but the hook 102a and the protrusion member 136 of the lid holding mechanism 131 are located not to contact with each other, and, also, at this point, the lid holding mechanism 131 does not perform a rotational movement operation.

FIG. 11 illustrates a state in which the hooks 102a to 102f are hooked to the lids 101a to 101f of the reagent containers 116 to 118. In FIG. 11, the hooks 102a to 102f are displaced to an engagement position in the state illustrated in FIG. 6 so as to be hooked to the corresponding lids 101a to 101f of the reagent containers 116 to 118. Also at this point, the lid holding mechanism is not rotationally moved.

FIG. 12 illustrates an intermediate state of an operation of opening all of the lids 101a to 101f of the reagent containers 116 to 118, and the hook part 104 is displaced in the opening direction so as to be moved to the upper position by driving the lid opening/closing drive device 106 in FIG. 4 in the state illustrated in FIG. 11.

At this time, as illustrated in FIG. 13, since an attractive force of the elastic member 137 is less than torque of the lid opening/closing drive device 106 in FIG. 4, the lid 101a pulled up by the hook 102a pushes up the protrusion member 136 of the lid holding mechanism 131 from the obliquely downward side so as to stretch the elastic member 137 and also to rotationally move the lid holding mechanism 131 in the counterclockwise direction.

FIG. 14 illustrates an operation of completely opening all of the lids 101a to 101f of the reagent containers 116 to 118, and the hook part 104 is in a state of being displaced in the opening direction so as to be moved to the upper position by further driving the lid opening/closing drive device 106 in FIG. 4 in the state illustrated in FIG. 12.

In this case, as illustrated in FIG. 15, the lid 101a pulled up by the hook 102a completely comes into contact with the protrusion member 136 of the lid holding mechanism 131. At this time, since the torque of the lid opening/closing drive device 106 in FIG. 4 is not applied, the lid 101a receives the pressing force of the elastic member 137 from the surface coming into contact with the protrusion member 136. Thus, the lid 101a is held by the protrusion member 136.

FIG. 16 illustrates an operation of closing all of the lids 101a to 101f of the reagent containers 116 to 118. As illustrated in FIG. 16, the hook part 104 is displaced in the closing direction so as to be moved to the lower position by driving the lid opening/closing drive device 106 in the state illustrated in FIG. 14.

At this time, the hook part 104 is moved to a slightly lower side than the position illustrated in FIG. 7 so as to press the lids 101a to 101f downward at basal parts of the hooks 102a to 102f, and thus the lids 101a to 101f of the reagent containers 116 to 118 are reliably closed.

In this case, as illustrated in FIG. 17, a holding force of the elastic member 137 is less than the torque of the lid opening/closing drive device 106 in FIG. 4. Thus, the lid 101a pulled up by the hook 102a is rotationally moved by the hook 102a in the closing direction.

Therefore, the lid 101a is closed while being slid on the surface of the protrusion member 136 of the lid holding mechanism 131, but, at this time, the protrusion member 136 of the lid holding mechanism 131 is rotationally moved in the clockwise direction by the attractive force of the elastic member 137, and thus the lid holding mechanism 131 is returned to the state illustrated in FIG. 6.

In a case where the hook part 104 is returned to the reference position illustrated in FIG. 7 in the state illustrated in FIG. 16, first, as illustrated in FIG. 8, the hooks 102a to 102f are displaced in the separation direction, the hook part 104 is displaced in the opening direction so as to be moved to the upper position, and the hooks 102a to 102f are displaced in the engagement direction so as to be returned to be oriented vertically downward.

FIGS. 7, 9, 11, 12, 14, 16 and 18 illustrate the sequence of simultaneously opening or closing the lids 101a to 101f of the six reagent containers 116 to 118, but, when the lids 101a to 101f are opened, the reagent suction probe 108 or the reagent stirring rod 109 illustrated in FIG. 4 accesses the open reagent containers.

For example, in a case where, among one set of the reagent containers 116 to 118, a solution containing magnetic particles which are easily immersed is put in the reagent container 116, it is necessary to stir the solution in the reagent container 116 with the reagent stirring rod 109 in FIG. 4 in order to dispense a uniform solution. This stirring requires a long period of time, and thus the reagent stirring rod 109 in FIG. 4 is required to access a reagent container for a longer period of time than the reagent suction probe 108 in FIG. 4.

In other words, there is a difference between the times required to access the reagent container 116 and the reagent containers 117 and 118 due to a difference between solutions. For example, even if the reagent stirring rod 109 in FIG. 4 accesses the reagent container 116 and the reagent suction probe 108 in FIG. 4 accesses the reagent container 117 at the same time, suction is completed during stirring.

Therefore, it is desirable that the lid 101b of the reagent container 117 in which suction of a reagent is completed is closed as soon as possible even during stirring of a reagent in the reagent container 116, and thus vaporization or deterioration of the reagent is prevented.

Although not particularly illustrated, the automated analyzer 10 in FIG. 1 is provided with a control device. The control device controls the lid opening/closing drive device 106 of the reagent container lid opening/closing mechanism 121 and the hook drive device on the basis of sample analysis request information, and opens the lid 101 of a corresponding reagent container when dispensing and stirring of a reagent are started. The control device closes the lid 101 of the corresponding reagent container when dispensing and stirring of the reagent are finished.

As mentioned above, in the automated analyzer 10, a plurality of hooks 102a to 102f are provided in the hook part 104, the hooks 102a to 102f are individually engaged with and disengaged from the lids 101a to 101f of the reagent containers 116 to 118, and the hook part 104 is displaced in the opening/closing direction of the lids 101a to 101f with the single lid opening/closing drive device 106. Thus, the lids 101a to 101f of the reagent containers 116 to 118 can be selectively opened or closed.

Consequently, lids of other reagent containers which are not required to be opened are not opened in order to open a lid of a target reagent container. For example, in a case where one process is finished earlier as when a stirring process and a dispensing process are performed together, lids can be closed in the order of the process being finished without waiting for the other process to be finished.

Therefore, it is possible to prevent vaporization or deterioration of a reagent by reducing open time of a reagent container which is not in use.

The lid holding mechanism 131 achieves the greatest effect during the above-described operation. For example, a case is assumed in which the lids 101b to 101f of the other reagent containers are closed while a lid of a specific reagent container, for example, the lid 101a is maintained to be open in the state illustrated in FIG. 14 in which the lids 101a to 101f of all the reagent containers are opened.

In this case, as illustrated in FIG. 18, in a state in which the hooks 102b to 102f are maintained at the engagement positions, the hook part 104 is moved in the closing direction by driving the lid opening/closing drive device 106, and the hook 102a is displaced in the separation direction such that the hook 102a does not interfere with the open lid 101a.

Consequently, in a state in which the lid 101a of the leftmost reagent container 116 is open, the lids 101b to 101f of the other reagent containers can be closed.

However, at this time, as illustrated in FIG. 20, since the opening of the hook 102a overlaps the rotational movement trajectory of the lid 101a of the reagent container centering on the fulcrum, there is a case where it is difficult for the hook 102a to hold the lid 101a of the reagent container.

In this case, the opening/closing spring 138 is provided to support an opening/closing operation of the lid 101a of the reagent container illustrated in FIG. 19, but a spring force becomes unstable over time with respect to even the opening/closing spring 138, and thus it cannot be said that sufficient supporting is possible.

As described above, stirring of a solution using the reagent stirring rod 109 requires a long period of time, and thus an open time of the lid 101a increases. Even while the lid 101a is open, other lids 101 are repeatedly opened and closed, and thus vibration due to opening and closing of the other lids is also applied to the lid 101a.

Thus, in a case where a state of a spring force being unstable occurs or the spring is damaged, the lid 101a cannot be held and is thus closed, and thus the device is stopped. As a result, there is concern that an analysis result may be delayed or a specimen sample may be lost.

Therefore, the protrusion member 136 of the lid holding mechanism 131 holds the lid 101a, and can thus stably hold the lid 101a of the reagent container in an open state. Thus, it is possible to prevent the lid 101a from being closed during stirring of a solution.

In other words, since the lid holding mechanism 131 is provided, the hook 102a may not hold the lid 101a, and thus the lid 101a is not influenced by opening/closing operations of the lids 101b to 101f of the other reagent containers in a case of performing the opening/closing operations of the lids 101b to 101f of the other reagent containers.

Consequently, even if opening/closing operations of the lids of other reagent containers are performed in a state in which the lid of the reagent container in which a reagent is being stirred is open, it is possible to stably hold the lid 101a of the reagent container in an open state without being influenced by the opening/closing operations of the lids of the other reagent containers.

Although not particularly illustrated, for example, even in a case where the number of hooks 102 is not the same as the number of reagent containers 116 to 118 which can be arranged at the dispensing/stirring position 113, and the lids 101 of a plurality of reagent containers 116 to 118 which are opening/closing targets may be selectively opened and closed with a single or a plurality of hooks, the lid holding mechanism 131 is in a state of holding the opened lid 101 (target A) of a reagent container after an opening operation of the lid 101 (this target lid is indicated by A) of a reagent container which is an opening/closing target in the reagent container lid opening/closing mechanism 121.

Thus, the reagent container lid opening/closing mechanism 121 can also perform an operation of being moved in order to open or close the lid 101 (target B) of another reagent container, completing an opening or closing operation on the lid 101 (target B) of another reagent container, and then being returned to the open lid 101 (target A) of the reagent container, and closing the lid 101 (target A).

Thus, in a device in which time can be taken for an operation process, for example, in a small analysis device, the lids 101 of a plurality of reagent containers 116 to 118 which are opening or closing targets can be selectively opened or closed with a single or a plurality of hooks 102 while the reagent container lid opening/closing mechanism 121 is being moved. Therefore, a space of the reagent container lid opening/closing mechanism 121 can be expected to be saved.

In the present embodiment, the description specialized for a reagent container has been made, but the present invention content can be adapted to a case where a container of which a lid is rotationally moved is used.

As mentioned above, the invention made by the present inventor has been described in detail on the basis of the above-described embodiment, but the present invention is not limited to the embodiment, and, needless to satisfy, various modifications may occur within the scope without departing from the sprit thereof.

The present invention is not limited to the above-described embodiment, and includes various modification examples. For example, the present invention has been described in detail for better understanding of the present invention, and is not limited to including all of the configurations described in the embodiment.

Some configurations of a certain embodiment may be replaced with configurations of other configurations, and configurations of other configurations may be added to configurations of a certain embodiment. The configurations of other embodiments may be added to, deleted from, and replaced with some of the configurations of each embodiment.

REFERENCE SIGNS LIST

10 AUTOMATED ANALYZER
11 MAGNETIC SEPARATION STIRRING DEVICE
12 INCUBATOR
13 REAGENT DISPENSING MECHANISM
14 REACTION DETECTION UNIT
15 SHIPPER
16 SPECIMEN DISPENSING NOZZLE
17 REACTION CONTAINER
18 SPECIMEN DISPENSING TIP

19 GRIPPER
20 TRANSPORT MECHANISM
21 REAGENT STIRRING MECHANISM
22 CONTAINER HOLDER
23 SPECIMEN CONTAINER
24 SPECIMEN TRANSPORT RACK
25 SPECIMEN DISPENSING TIP HOLDER
26 TIP ATTACHMENT LOCATION
27 SPECIMEN DISPENSING LOCATION
28 NOZZLE PART
100 CASSETTE
101 LID
102 HOOK
103 HOOK SHAFT
104 HOOK PART
105 ARM
106 LID OPENING/CLOSING DRIVE DEVICE
107 UNIT BASE
108 REAGENT SUCTION PROBE
109 REAGENT STIRRING ROD
110 OUTER CIRCUMFERENTIAL DISK
111 INNER CIRCUMFERENTIAL DISK
113 DISPENSING/STIRRING POSITION
114 FRAME
115 REAGENT REFRIGERATOR
115a UPPER COVER
116 REAGENT CONTAINER
117 REAGENT CONTAINER
118 REAGENT CONTAINER
120 REAGENT DISK
121 REAGENT CONTAINER LID OPENING/CLOSING MECHANISM
131 LID HOLDING MECHANISM
132 INNER CIRCUMFERENTIAL DISK BASE
133 HOLDING MECHANISM BASE PORTION
134 BEARING
135 HOLDING DRIVE PART
136 PROTRUSION MEMBER
137 ELASTIC MEMBER
138 OPENING/CLOSING SPRING

The invention claimed is:

1. An automated analyzer comprising:
a reagent refrigerator that cold-insulates one or more reagents stored in one or more containers, the one or more containers each having a corresponding lid which is rotationally movable to be opened and closed;
wherein the reagent refrigerator includes
a container holder that is mounted with a plurality of the containers;
a lid opening/closing mechanism that rotationally moves the lids of the containers mounted in the container holder so as to open and close the lids, and
a lid holding mechanism that comes into contact with a part of a first lid of a first container of the one or more containers in a state in which the lids are opened by the lid opening/closing mechanism;
wherein the lid holding mechanism includes
a holding mechanism base part that is fixed to the reagent refrigerator;
a holding drive part that has a protrusion, the protrusion is rotationally movable in a direction which is different from a rotational movement direction of the lids, and the protrusion centering on a support pin, so as to come into contact with the first lid to maintain the first lid in the opened position; and
an elastic member that has one end fixed to the holding mechanism base part and the other end fixed to the holding drive part, and generates a bias force with respect to the holding drive part; and
wherein, in a case where the first lid is in the closed position, the protrusion of the holding drive part does not come in contact with the first lid, in a case where the first lid transitions from the closed state to the opened state, the holding drive part comes into contact with the first lid, and is rotationally moved centering on the support pin to a position where the first lid is not hindered from being rotationally moved when an external force is applied to the holding drive part, and, in a case where the first lid is in the opened state, the holding drive part rotationally moves the protrusion to a position to maintain the first lid in the opened position due to a biasing force of the elastic member exerted on the holding drive part.

2. The automated analyzer according to claim 1, wherein the lid holding mechanism holds the first lid of a container located at the opened position where dispensing and stirring of a reagent in the first container is performed.

3. The automated analyzer according to claim 2, wherein the lid opening/closing mechanism closes the lids of the one or more containers not held by the lid holding mechanism while the lid holding mechanism is holding the first lid of the first container in the opened position.

4. The automated analyzer according to claim 2, wherein the first container of which the first lid is held by the lid holding mechanism in the opened position is a container storing a first reagent to be stirred by a reagent stirring rod.

5. The automated analyzer according to claim 4, wherein the lid opening/closing mechanism closes the lids of the one or more containers storing the one or more reagents which are not stirred while the first reagent stored in the first container in the opened position is being stirred.

6. The automated analyzer according to claim 1, wherein the elastic member is a tension spring.

* * * * *